(12) United States Patent
Kemmerer et al.

(10) Patent No.: US 10,124,159 B2
(45) Date of Patent: Nov. 13, 2018

(54) ORAL MUCOSAL ELECTROPORATION DEVICE AND USE THEREOF

(75) Inventors: Stephen V Kemmerrer, San Diego, CA (US); Kate Broderick, San Diego, CA (US); Jay McCoy, San Diego, CA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 389 days.

(21) Appl. No.: 13/641,977

(22) PCT Filed: Apr. 28, 2011

(86) PCT No.: PCT/US2011/034277
§ 371 (c)(1),
(2), (4) Date: Oct. 18, 2012

(87) PCT Pub. No.: WO2011/137221
PCT Pub. Date: Nov. 3, 2011

(65) Prior Publication Data
US 2013/0041310 A1    Feb. 14, 2013

Related U.S. Application Data

(60) Provisional application No. 61/328,868, filed on Apr. 28, 2010.

(51) Int. Cl.
*A61N 1/04* (2006.01)
*A61N 1/32* (2006.01)
*C12M 1/42* (2006.01)
*C12N 13/00* (2006.01)
*A61N 1/05* (2006.01)

(52) U.S. Cl.
CPC ........... *A61N 1/0424* (2013.01); *A61N 1/327* (2013.01); *C12M 35/02* (2013.01); *C12N 13/00* (2013.01); *A61N 1/0548* (2013.01)

(58) Field of Classification Search
CPC ......... A61N 1/424; A61N 1/548; A61N 1/327
USPC ................... 604/20, 21, 500; 17/20, 21, 500
See application file for complete search history.

(56) References Cited

U.S. PATENT DOCUMENTS

| | | | | |
|---|---|---|---|---|
| 5,318,514 A | * | 6/1994 | Hofmann | ............... A61N 1/303 604/20 |
| 5,810,762 A | * | 9/1998 | Hofmann | ........................ 604/20 |
| 6,006,130 A | * | 12/1999 | Higo | .................... A61N 1/0436 604/20 |
| 6,230,051 B1 | * | 5/2001 | Cormier | ............. A61B 5/15142 600/573 |
| 6,678,556 B1 | | 1/2004 | Nolan | |
| 6,972,013 B1 | * | 12/2005 | Zhang | .................... A61N 1/327 604/20 |
| 6,978,172 B2 | | 12/2005 | Mori | |

(Continued)

FOREIGN PATENT DOCUMENTS

WO    2009/091578    7/2009

*Primary Examiner* — Kevin C Sirmons
*Assistant Examiner* — Leah Swanson
(74) *Attorney, Agent, or Firm* — Baker & Hostetler LLP

(57) ABSTRACT

The present invention relates to electroporation (EP) devices that are able to generate an electroporation causing electrical field at the mucosal layer, and preferably in a tolerable manner. Further, it includes the generation of a protective immune response, cellular and/or humoral, using the oral EP device along with a genetic construct that encodes an immunogenic sequence.

15 Claims, 20 Drawing Sheets

(56) References Cited

U.S. PATENT DOCUMENTS

2008/0058706 A1    3/2008  Zhang
2009/0131905 A1*   5/2009  Allen et al. .................. 604/501

* cited by examiner

Periphery

BAL

ORAL MUCOSAL ELECTROPORATION DEVICE AND USE THEREOF

CROSS-REFERENCE TO RELATED APPLICATIONS SECTION

This application is a 371 National stage entry of International Application No. PCT/US2011/034277, filed Apr. 28, 2011, and claims the benefit of U.S. Provisional Application No. 61/328,868, filed Apr. 28, 2010, the contents of which are incorporated herein by reference.

FIELD OF INVENTION

The present invention relates to electroporation devices that enable the delivery of therapeutics to a subject.

BACKGROUND

A vast majority of human pathogens are known to initiate infections at mucosal surfaces, thus, making the gastrointestinal, urogenital and respiratory tracts major routes of entry into the body. As a result, the other primary way to contract an infection is through blood-borne routes such injections, transfusions and bites. Examples of mucosally-infecting agents include cold viruses, influenza, food poisoning agents tuberculosis, sexually transmitted diseases, cholera, diphtheria and the plague.

The mucous membranes are one of the largest organs of the body. Collectively, they cover a surface area of more than 400 $m^2$ (equivalent to one and half tennis courts) and comprise the linings of the gastrointestinal, urogenital and respiratory tracts. These mucosal surfaces, while located inside the body, are actually a physical barrier between the outside and the sterile interior cavity of the body known as the "systemic" environment. Critical nutrients, oxygen and other molecules are constantly taken up across these mucosal barriers; however, another important function of the mucous is to keep invading pathogens out. Daily these mucous membranes are bombarded by outside elements and it is up to the unique immune system of the mucous to determine what is potentially harmful and what is beneficial.

The importance of mucosal immunology lies in the interplay between the mucosal response and the systemic immune response. Several studies have demonstrated that stimulating the immune system systemically (i.e. via injection or blood-borne routes) results in the production of protective antibody and T cells only within the sterile, internal environment of the body—no mucosal response is generated. On the other hand, stimulation of the mucosal immune response can result in production of protective B and T cells in both mucosal and systemic environments so that infections are stopped before they get into the body.

The mucous membranes produce a special type of antibody called secretory IgA or sIgA. The mucous membranes are bathed in huge quantities of sIgA, which act as a first line of defense to neutralize invading pathogens. Experimental evidence shows that the presence of sIgA correlates with resistance to infection by various pathogens, including bacteria, viruses, parasites and fungi. It has also been shown to neutralize viruses and prevent their adherence to the epithelial cells lining the mucous (thereby preventing infection) as well as mediating excretion of pathogens and preventing the assembly of mature virus particles.

Another important component of mucosal immunity is the T cell-mediated immune response. T-cells that specifically recognize pathogens can help antibodies to clear the infection or directly kill the invader themselves. T cells produced in the mucous are capable of traveling throughout the mucosal tissues through special "homing" receptors on their membranes. This means that if an immune response is generated in the gastrointestinal lining, T cells produced there can travel to other mucosal sites, for example, the lungs or nasal cavity, providing protection over a large area.

Despite the important role of the mucosal surface, only a handful of vaccines specifically target this area of the immune system, thus there remains a need for vaccines that are directed toward the mucosal surface to provide protective immune responses at the mucosal tissue.

SUMMARY OF THE INVENTION

There are provided electroporation devices capable of electroporating cells of a mucosal membrane of a mammal. Such devices include an electrode microneedle plate, a counter electrode plate, a main housing and an energy source. The main housing is in physical communication with said microneedle plate and counter electrode plate, wherein the main house is in fluid communication with a syringe capable of storing a pharmaceutical formulation for delivery. The energy source is in electrical communication with the microneedle plate and capable of generating an electric potential and delivering the electric potential to the cells through the microneedle plate.

In another aspect, there are provided methods of administering a pharmaceutical formulation to cells of a mucosal membrane of a mammal with the provided devices. The methods comprise contacting said microneedle plate to said mucosal membrane, delivering said pharmaceutical formation to said mucosal membrane, and applying an electroporation causing electrical pulse to the mucosal membrane through the microneedle plate, which was generated by said energy source.

BRIEF DESCRIPTION OF THE DRAWINGS

FIG. 6 displays graphs and images that show a strong immune response was generated.

FIG. 8 displays graph that show that CTACK Elicits High Levels of Cytokine Secreting CD8+ T cells in the Lung.

FIG. 11 displays graphs that show HAI titer levels in serum from macaques that were immunized with SynCon™ influenza vaccine. Results shown are two weeks post-second immunization.

DETAILED DESCRIPTION OF THE INVENTION

Figure 1:
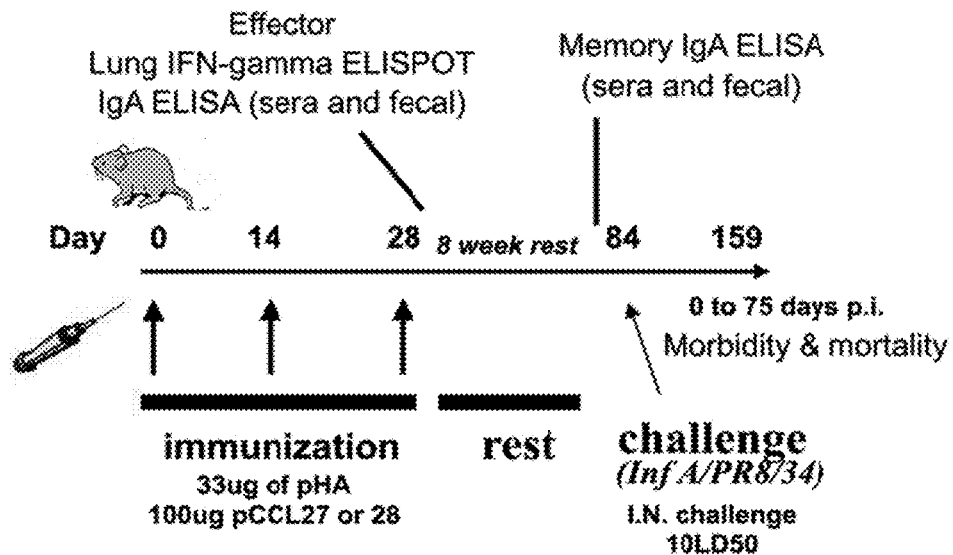
FIG. 1 shows an immunization (via standard injection) and challenge timeline to be performed in a mouse.
Figure 2:
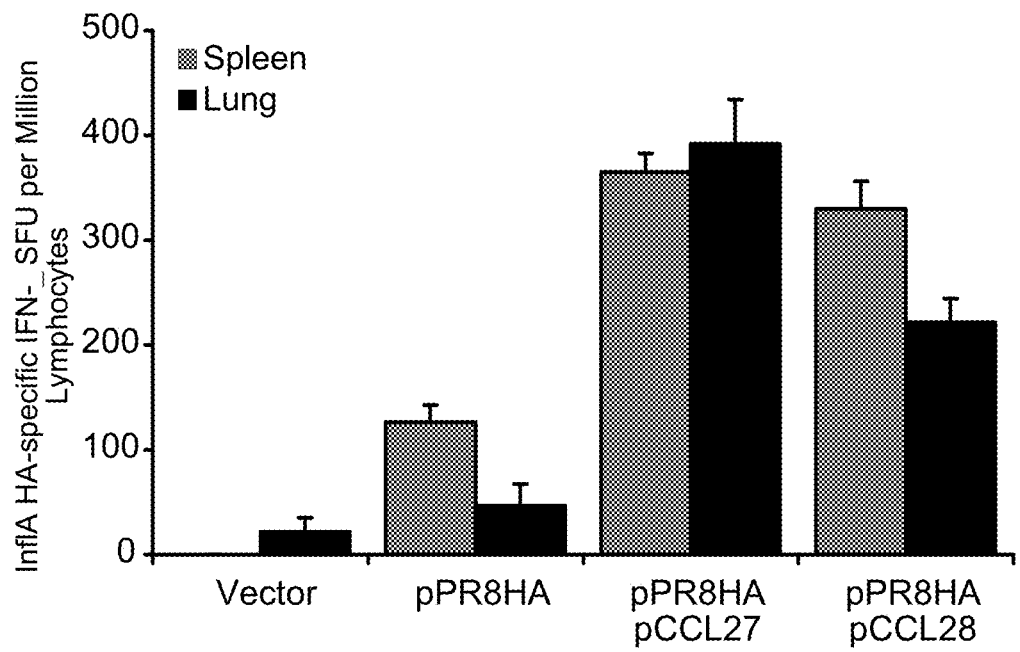
FIG. 2 displays a graph that shows that chemokine adjuvants induce cellular immunity specific against influenza APR/8/34 in a mouse model of mucosal lung infection.
Figure 3A:
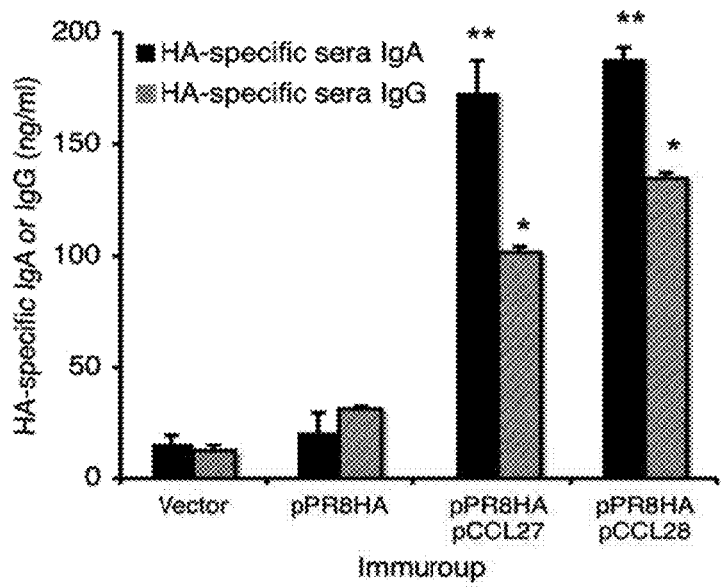
FIG. 3a displays a graph that shows InfluenzaA/PR/8/34-specific serum long-lived IgA and IgG pre-challenge.
Figure 3B:
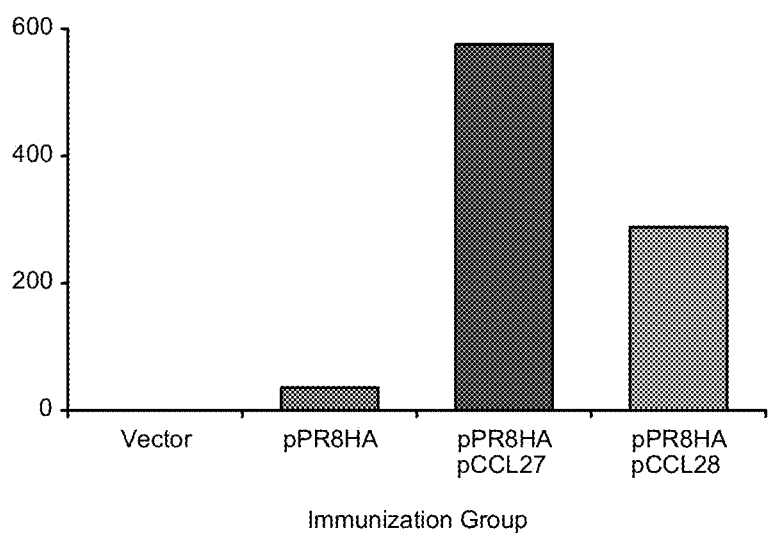
FIG. 3b displays a graph that shows InfluenzaA/PR/8/34 neutralizing antibody pre-challenge.
Figure 3C:
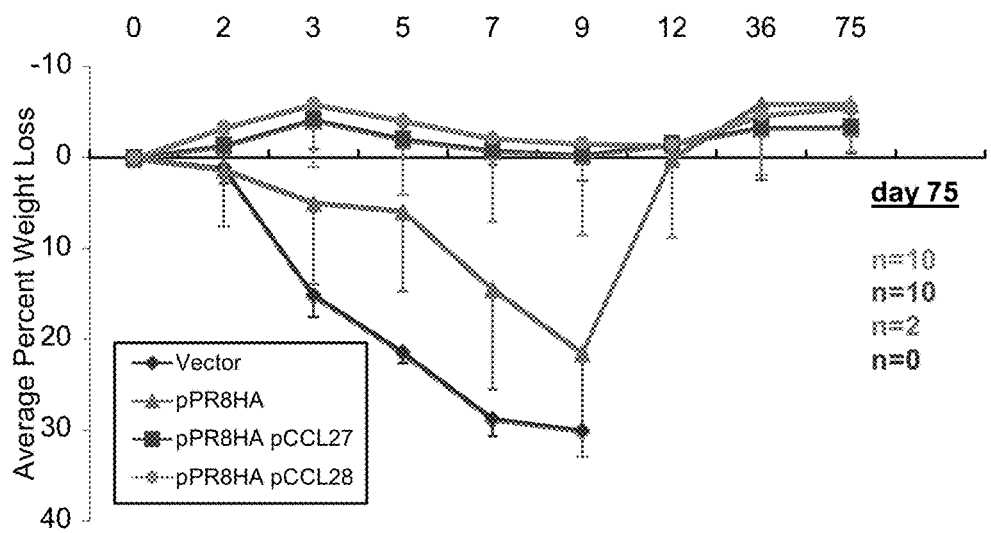
FIG. 3c displays a line graph that shows average weight loss over days.
Figure 3D:
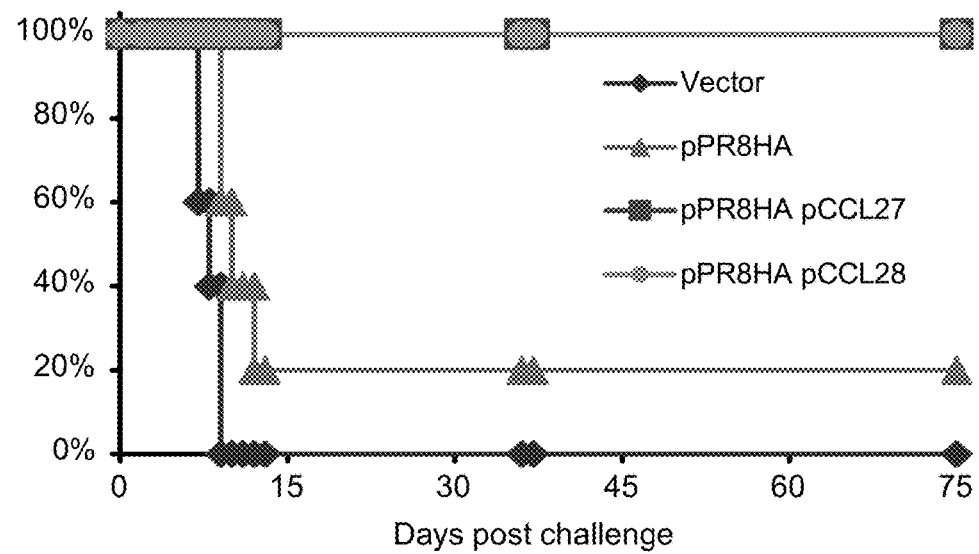
FIG. 3d displays a line graph that shows the various survival rates after challenge.
Figure 4:
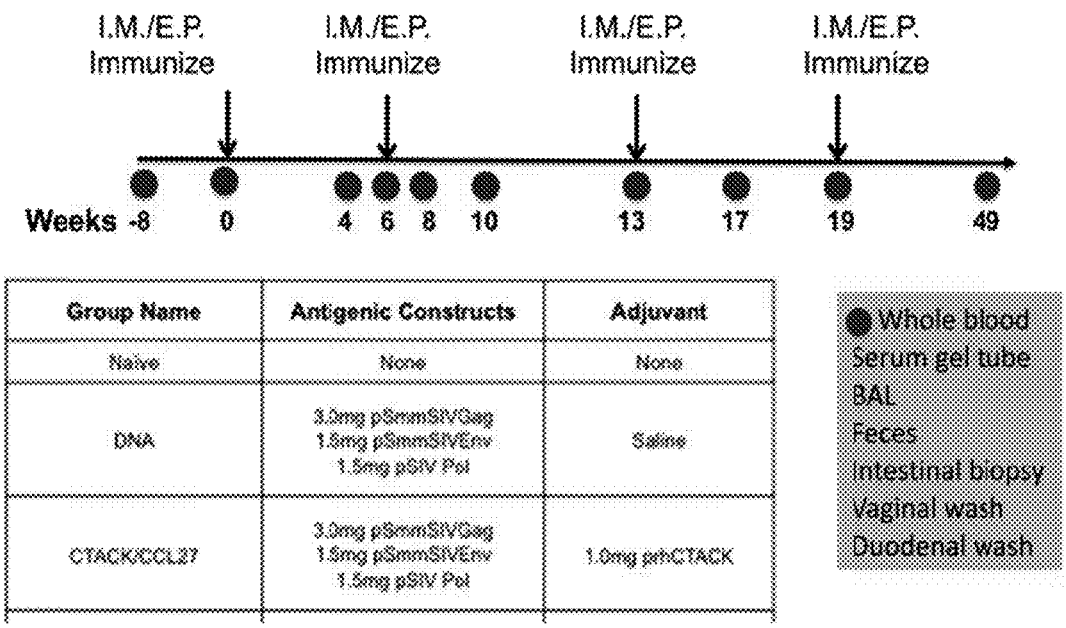
FIG. 4 displays a timeline and additional information about Indian Rhesus Macaques Immunization Schedule.
Figure 5:
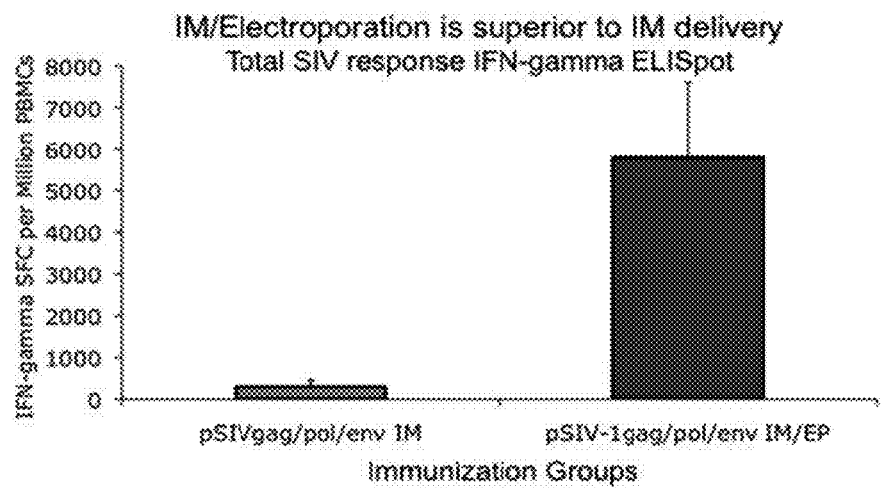
FIG. 5 displays a graph that shows ELISpot data from known IM (intramuscular)/EP (electroporation) delivery of DNA vaccine is superior to IM delivery alone.
Figure 6A:
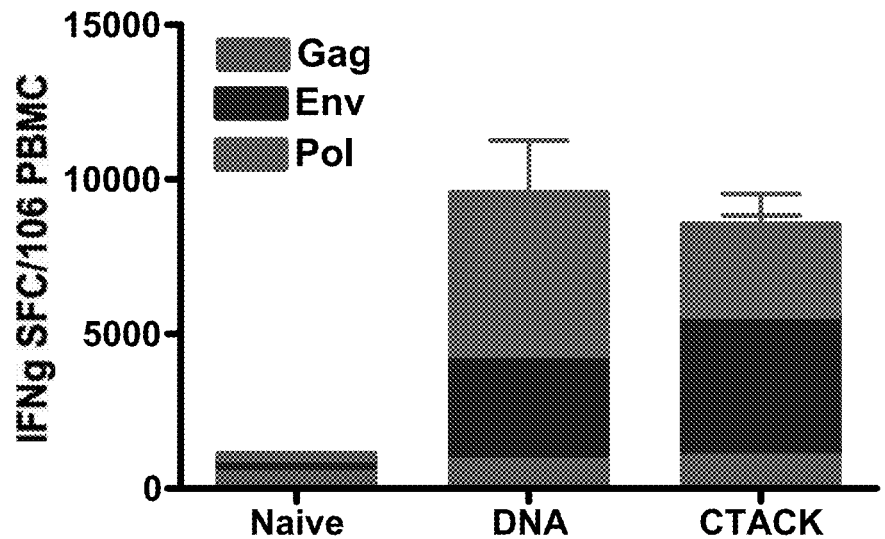
FIG. 6a displays a graph that shows ELISpot data.
Figure 6B:
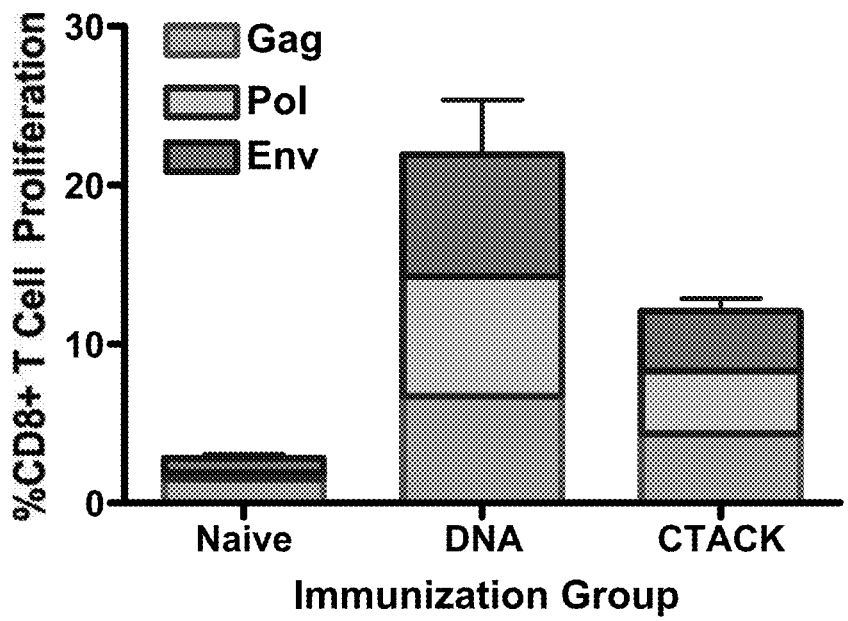
FIG. 6b displays a graph that shows levels of T cell proliferation.
Figure 6C:
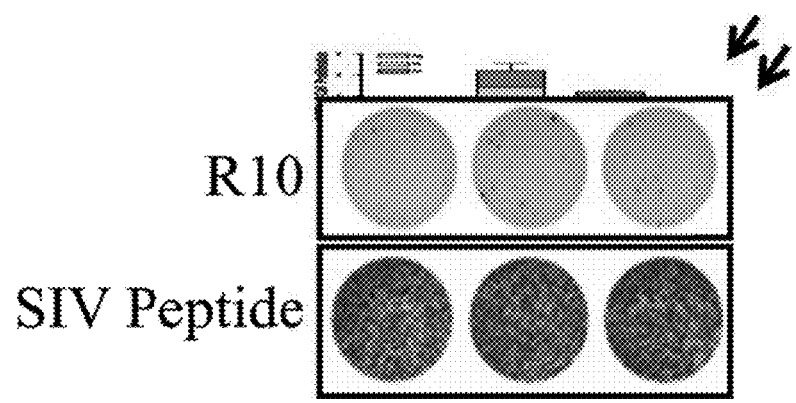
FIG. 6c shows plates from R10 or SIV peptide cultures.
Figure 6D:
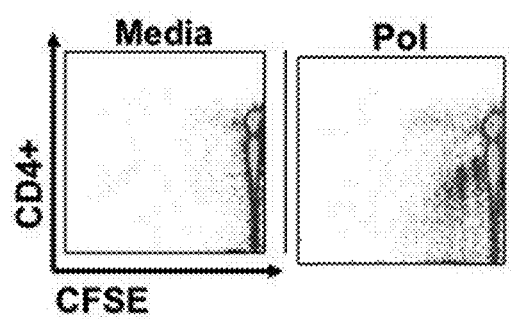
FIG. 6d shows graphs that suggest CFSE Proliferation FIG. 7 displays graphs that show that CTACK Co-immunization Augments Cytokine Secretion by CD4+ T cells in the BAL.
Figure 7A:
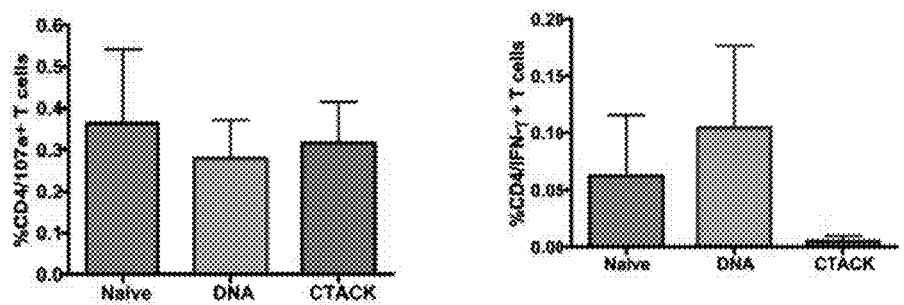
FIG. 7a displays graphs that show the cellular response in the periphery.
Figure 7B:
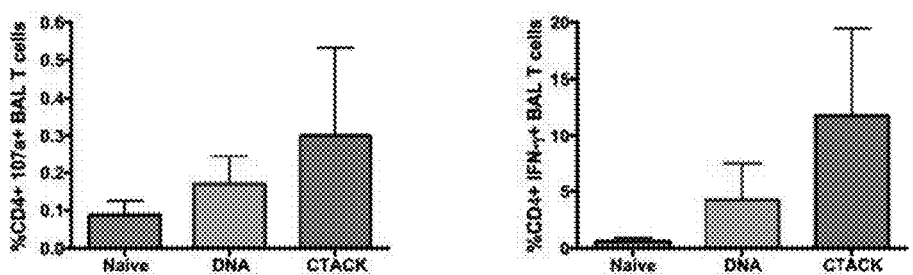
FIG. 7b displays graphs that show the cellular response in BAL.
Figure 8A:
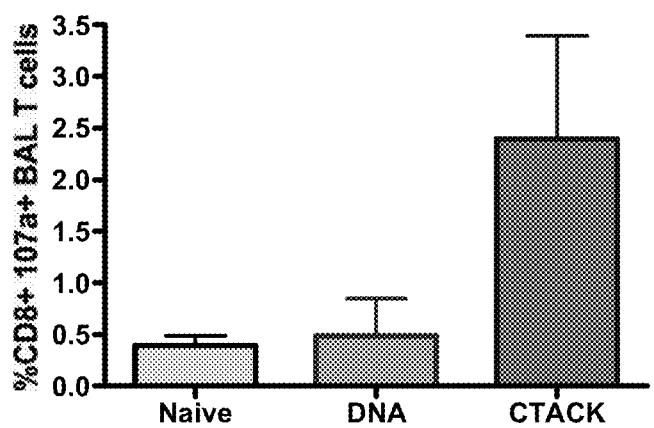
FIG. 8a displays a graph that shows the 107a+ CD8+ levels.
Figure 8B:
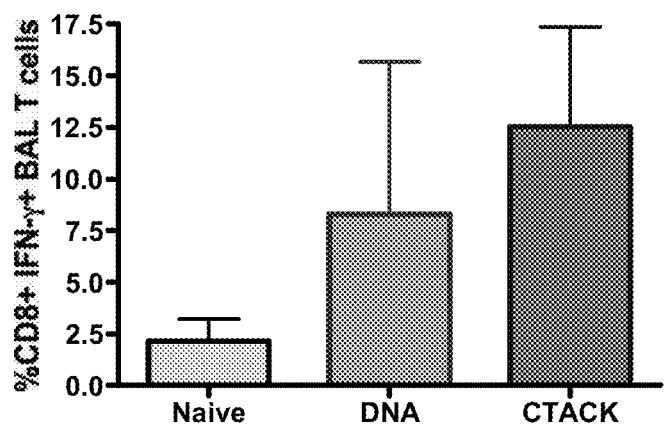
FIG. 8b displays a graph that shows the IFN-gamma CD+ levels.
Figure 8C:
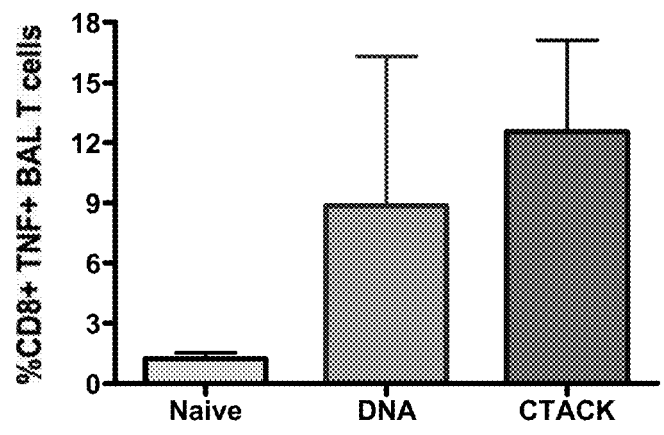
FIG. 8c displays a graph that shows the TNF+CD8+ levels.
Figure 8D:
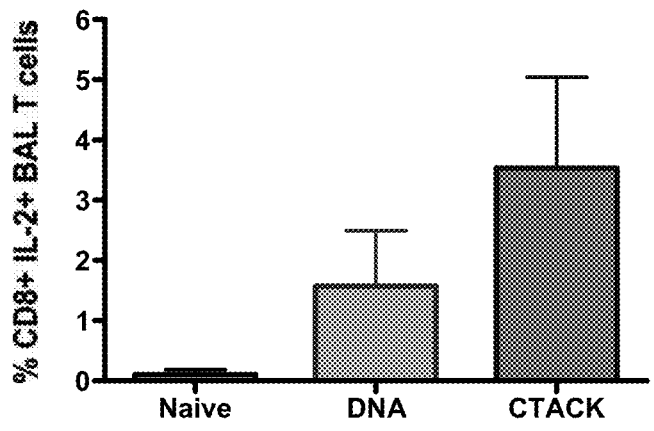
FIG. 8d displays a graph that shows IL-2+ CD8+ levels.
Figure 9:
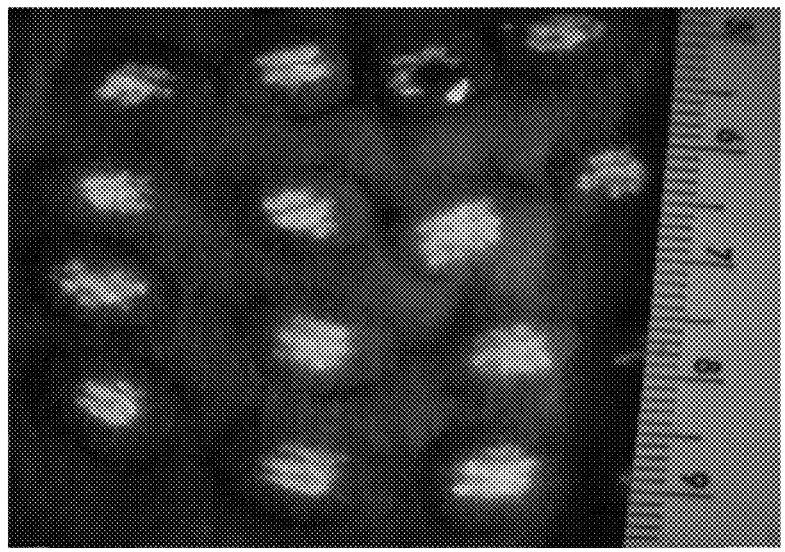
FIG. 9 displays a photo that shows positive GFP expression by way of fluorescence.
Figure 10:
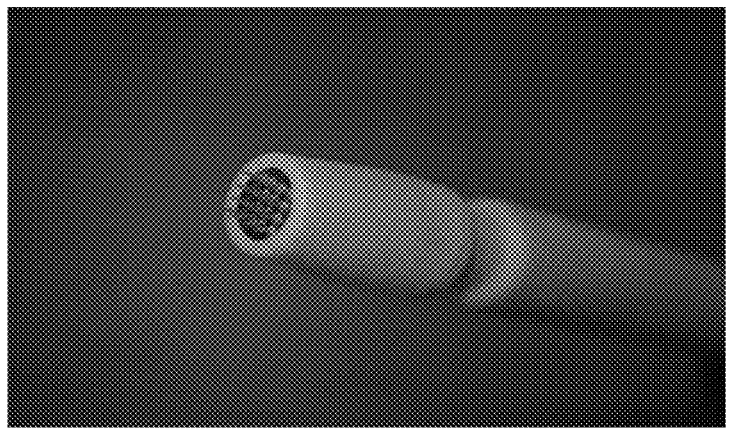
FIG. 10 displays a 4×4 array (Inovio Pharmaceuticals, Inc., Blue Bell, Pa.)
Figure 11A:
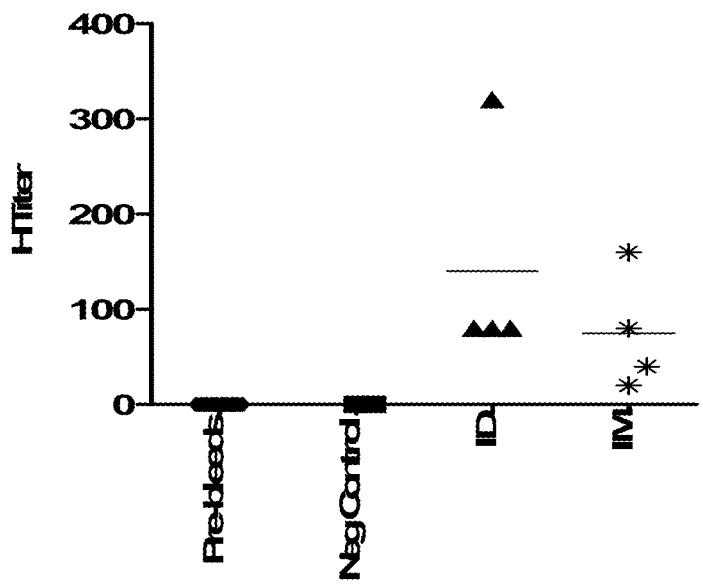
FIG. 11a HAI titers with respect to A/H1N1/Mexico/2009 strain.
Figure 11B:
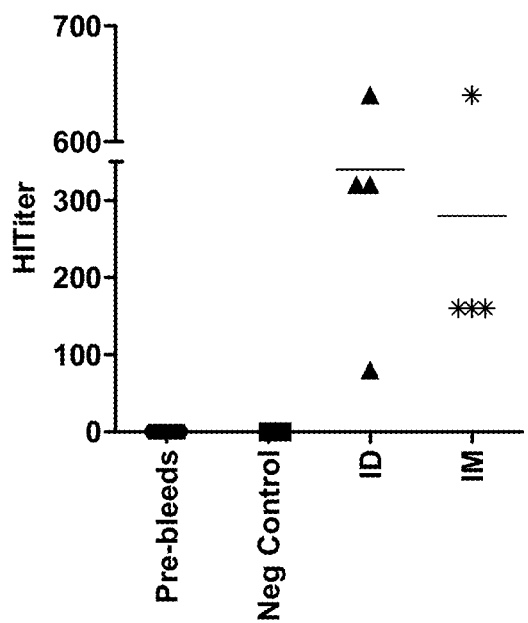
FIG. 11b HAI titers with respect to A/H1N1/New Caledonia.
Figure 12A:
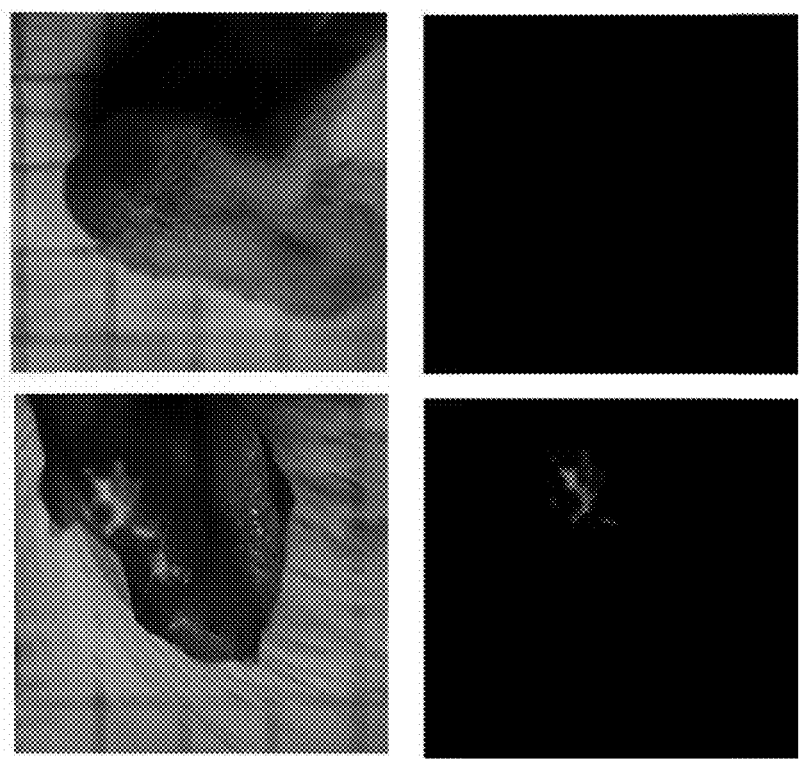
FIG. 12a displays photos that show GFP expression in guinea pig oral mucosal tissue following shallow injection of GFP plasmid and electroporation Whole cheek mounts were harvested 3 days post-treatment and viewed under a fluorescent microscope to determine positive GFP expression.
Figure 12B:
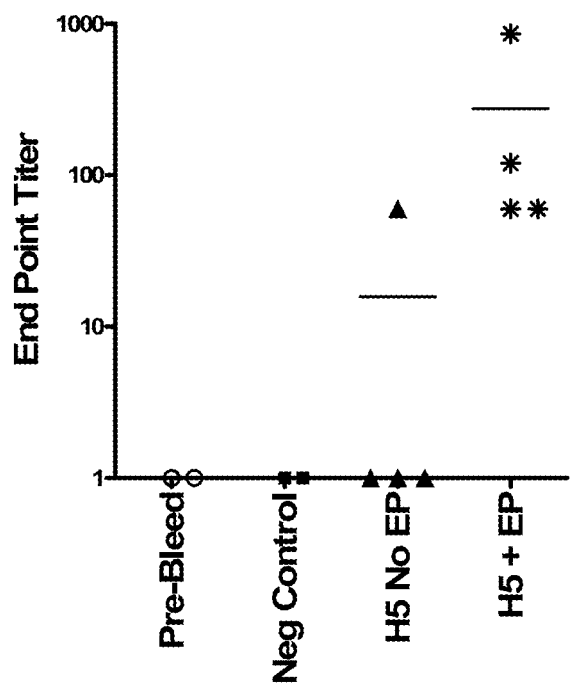
FIG. 12b displays a graph that shows H5-specific IgA titers following 3 immunizations in the guinea pig.
Figure 13:
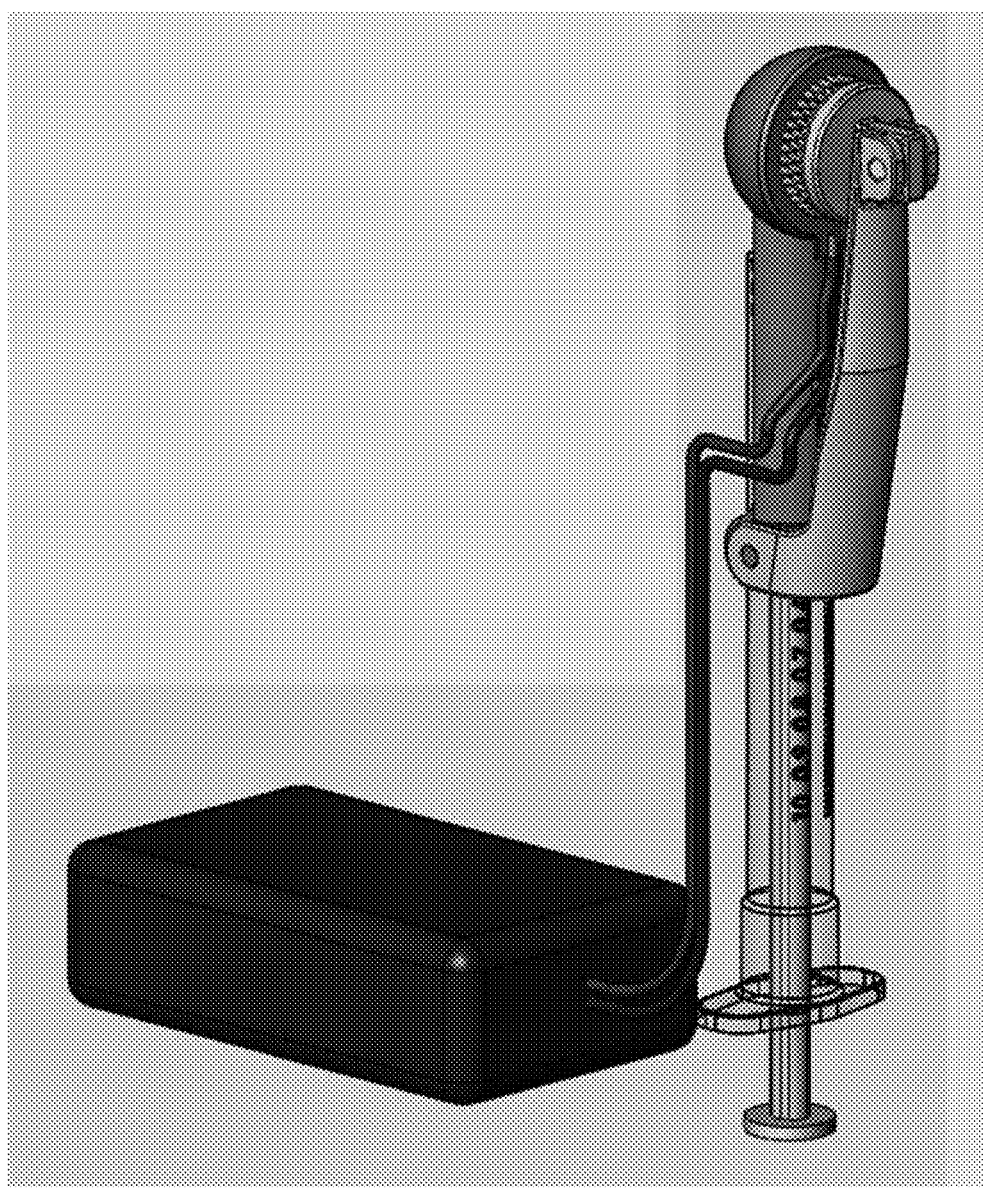
FIG. 13 is a ¾ view of an oral electroporation/injection device comprising: a pulse generator, an injection and an electroporation device.
Figure 14:
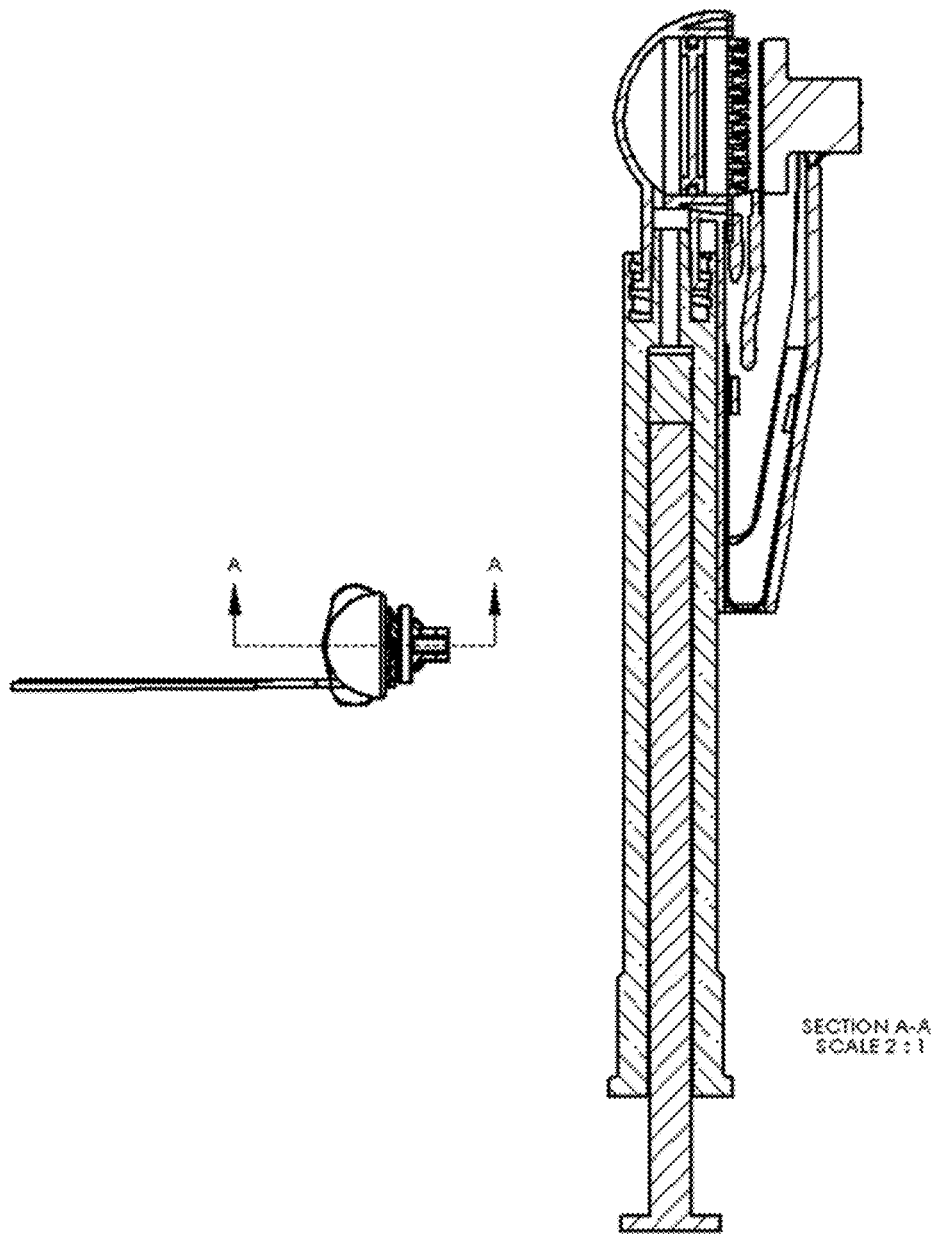
FIG. 14 is a drawing showing a vertical cross-section A-A of the oral electroporation/injection device.

There are provided electroporation devices capable of electroporating cells of a mucosal membrane of a mammal. Such devices include an electrode microneedle plate, a counter electrode plate, a main housing and an energy source. The main housing is in physical communication with said microneedle plate and counter electrode plate (item #4), wherein the main house is in fluid communication with a syringe capable of storing a pharmaceutical formulation for delivery. The energy source (item #10) is in electrical communication with the microneedle plate and capable of generating an electric potential and delivering the electric potential to the cells through the microneedle plate. In an embodiment, there is also a piston in physical communication between said main housing and said microneedle plate. The piston is actuatable and by actuating can cause even distribution of the pharmaceutical formulation through the microneedle plate.

In one aspect of the invention, there are provided oral electroporation (EP) devices that are able to generate an electroporation causing electrical field at the mucosal layer, and preferably in a tolerable manner. In one embodiment of this aspect, there is an oral mucosal injection and electroporation device (OM-I/EP) that is adapted to perform delivery of therapeutic (or prophylactic) formulations, such as DNA vaccines, and the transfection into the mucosal tissue/cells on the inside of the mouth. During a DNA vaccination procedure the device would be affixed across the cheek area of the patient. The main body with the main electrode micro-needle plate feature on the inside of the mouth and the return electrode plate clamp feature adjacent, on the outside of the cheek. The DNA vaccine would be injected through the micro-needle plate; this would then be followed by low voltage EP pulses applied to that same electrode microneedle plate, this design co-locates the DNA vaccine and the electroporation to the same area. Research has shown that the co-location of DNA vaccine and EP to be very important in the amount of DNA vaccine transfection into the surrounding cells.

In some embodiments, the microneedles of the microneedle plate are made from electrically conductive materials comprising gold and silver plated brass, gold and silver plated copper, stainless steel, or titanium, or other commonly known conductive metal or metal-like material. In some embodiments, the energy source is capable of delivering through the microneedle plate to the cells of the mucosal membrane at least one pulse of electrical energy having characteristics of between 1V and 30V, 2 mA and 100 mA, or 1 mS and 250 mS. The mucosal membrane or mucosal tissue can be buccal, nasal, esophageal, rectal, vaginal, vulva, intestinal, bowel, stomach, bladder, urinary tract, or eye tissue, and preferably buccal tissue, e.g., the inner surface of the mouth.

In another aspect, there are provided methods of administering a pharmaceutical formulation to cells of a mucosal membrane of a mammal with the provided devices. The methods comprise contacting said microneedle plate to said mucosal membrane, delivering said pharmaceutical formation to said mucosal membrane, and applying an electroporation causing electrical pulse to the mucosal membrane through the microneedle plate, which was generated by said energy source.

During in vivo electroporation, electric pulses are applied directly to the tissue to enhance uptake of extracellular molecules. Present types of in vivo EP are done with very high volt/centimeter electrical field strengths, using such large electrical field strengths is would be painful to the patient in mucosal tissue due to the high density of nerves. With the current OM-I/EP devices, they can be equipped to deliver very low field strength EP, such as using the low energy electrical pulses that were applied at intradermal (ID) injection sites, which were described in an earlier filed, co-owned PCT application entitled, "CONTACTLESS ELECTROPERMEABILIZATION ELECTRODE AND METHOD" having application number PCT/US10/31431, filed Apr. 16, 2010, and incorporated by reference herein in its entirety. Such intradermal EP can be performed with very low voltages and with minimal to no pain to the patient. In early experiments on mucosal tissues these lower EP field strengths have shown transfection into mucosal tissue with similar results (data not shown). The EP parameters can include voltages ranging from 0.1 volts (V) to 30 V, 0.1 V to 20 V, 0.1 V to 15 V, 0.1 V to 10 V, 0.1 V to 9 V, 0.1 V to 8 V, 0.1 V to 7 V, 0.1 V to 6 V, 0.1 V to 5 V, 0.1 V to 4 V, 0.1 V to 3 V, 0.1 V to 2 V, 0.1 V to 1 V, 2 V to 30 V, 2 V to 20 V, 2 V to 15 V, 2 V to 10 V, 2 V to 9 V, 2 V to 8 V, 2 V to 7 V, 2 V to 6 V, 2 V to 5 V, 2 V to 4 V, 2 V to 3 V, 4 V to 30 V, 4 V to 20 V, 4 V to 15 V, 4 V to 10 V, 4 V to 9 V, 4 V to 8 V, 4 V to 7 V, 4 V to 6 V, 4 V to 5 V, 6 V to 30 V, 6 V to 20 V, 6 V to 15 V, 6 V to 10 V, 6 V to 9 V, 6 V to 8 V, 8 V to 30 V, 8 V to 20 V, 8 V to 15 V, 8 V to 10 V, 8 V to 9 V, 10 V to 30 V, 10 V to 20 V, or 10 V to 15 V; and currents ranging from 2 mA to 100 mA, 3 mA to 100 mA, 4 mA to 100 mA, 5 mA to 100 mA, 6 mA to 100 mA. 7 mA to 100 mA, 8 mA to 100 mA, 9 mA to 100 mA, 10 mA to 100 mA, 20 mA to 100 mA, 30 mA to 100 mA, 40 mA to 100 mA, 60 mA to 100 mA, 80 mA to 100 mA, 2 mA to 80 mA, 3 mA to 80 mA, 4 mA to 80 mA, 5 mA to 80 mA, 6 mA to 80 mA, 7 mA to 80 mA, 8 mA to 80 mA, 9 mA to 80 mA, 10 mA to 80 mA, 20 mA to 80 mA, 30 mA to 80 mA, 40 mA to 80 mA, 60 mA to 80 mA, 2 mA to 60 mA, 3 mA to 60 mA, 4 mA to 60 mA, 5 mA to 60 mA, 6 mA to 60 mA, 7 mA to 60 mA, 8 mA to 60 mA, 9 mA to 60 mA, 10 mA to 60 mA, 20 mA to 60 mA, 30 mA to 60 mA, 40 mA to 60 mA, 2 mA to 40 mA, 3 mA to 40 mA, 4 mA to 40 mA, 5 mA to 40 mA, 6 mA to 40 mA, 7 mA to 40 mA, 8 mA to 40 mA, 9 mA to 40 mA, 10 mA to 40 mA, 20 mA to 40 mA, 30 mA to 40 mA, 2 mA to 30 mA, 3 mA to 30 mA, 4 mA to 30 mA, 5 mA to 30 mA, 6 mA to 30 mA, 7 mA to 30 mA, 8 mA to 30 mA, 9 mA to 30 mA, 10 mA to 30 mA, 20 mA to 30 mA, 2 mA to 20 mA, 3 mA to 20 mA, 4 mA to 20 mA, 5 mA to 20 mA, 6 mA to 20 mA, 7 mA to 20 mA, 8 mA to 20 mA, 9 mA to 20 mA, 10 mA to 20 mA, 2 mA to 10 mA, 3 mA to 10 mA, 4 mA to 10 mA, 5 mA to 10 mA, 6 mA to 10 mA, 7 mA to 10 mA, 8 mA to 10 mA, 9 mA to 10 mA, 2 mA to 9 mA, 3 mA to 9 mA, 4 mA to 9 mA, 5 mA to 9 mA, 6 mA to 9 mA. 7 mA to 9 mA. 8 mA to 9 mA, 2 mA to 8 mA, 3 mA to 8 mA, 4 mA to 8 mA, 5 mA to 8 mA, 6 mA to 8 mA. 7 mA to 8 mA, 2 mA to 7 mA, 3 mA to 7 mA, 4 mA to 7 mA, 5 mA to 7 mA, 6 mA to 7 mA. 2 mA to 6 mA, 3 mA to 6 mA, 4 mA to 6 mA, 5 mA to 6 mA, 2 mA to 5 mA, 3 mA to 5 mA, 4 mA to 5 mA, 2 mA to 4 mA, or 3 mA to 4 mA. In some embodiments the EP parameters used range from 30 volts and 100 mA on the high end to 2 volts and 2 mA on the low end. For EP delivery, the desired tissue received two (2) pulses 100 ms each with a 100 ms delay between pulses.

Figure 15:
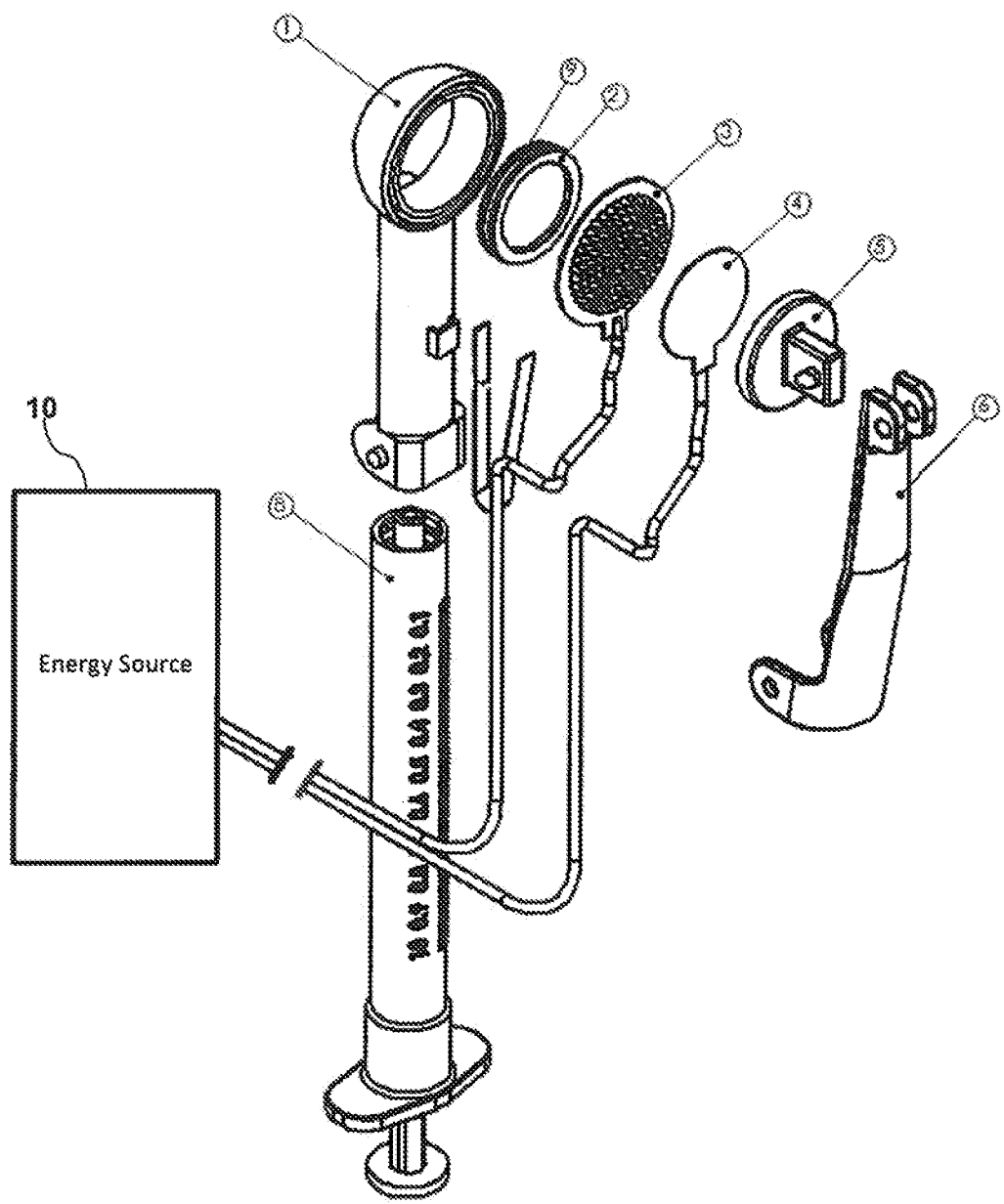
FIG. 15 is an exploded assembly of the electroporation/injection device.
Figure 16:
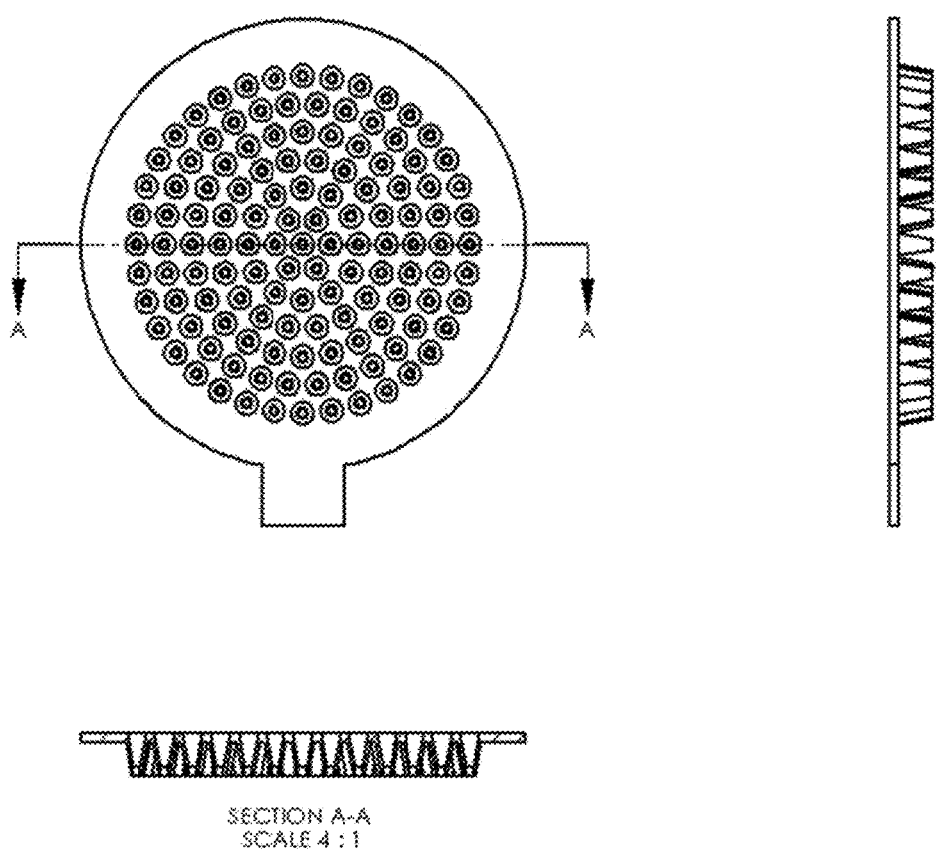
FIG. 16 is the main electrode micro-needle plate of the electroporation/injection device.
Figure 17:
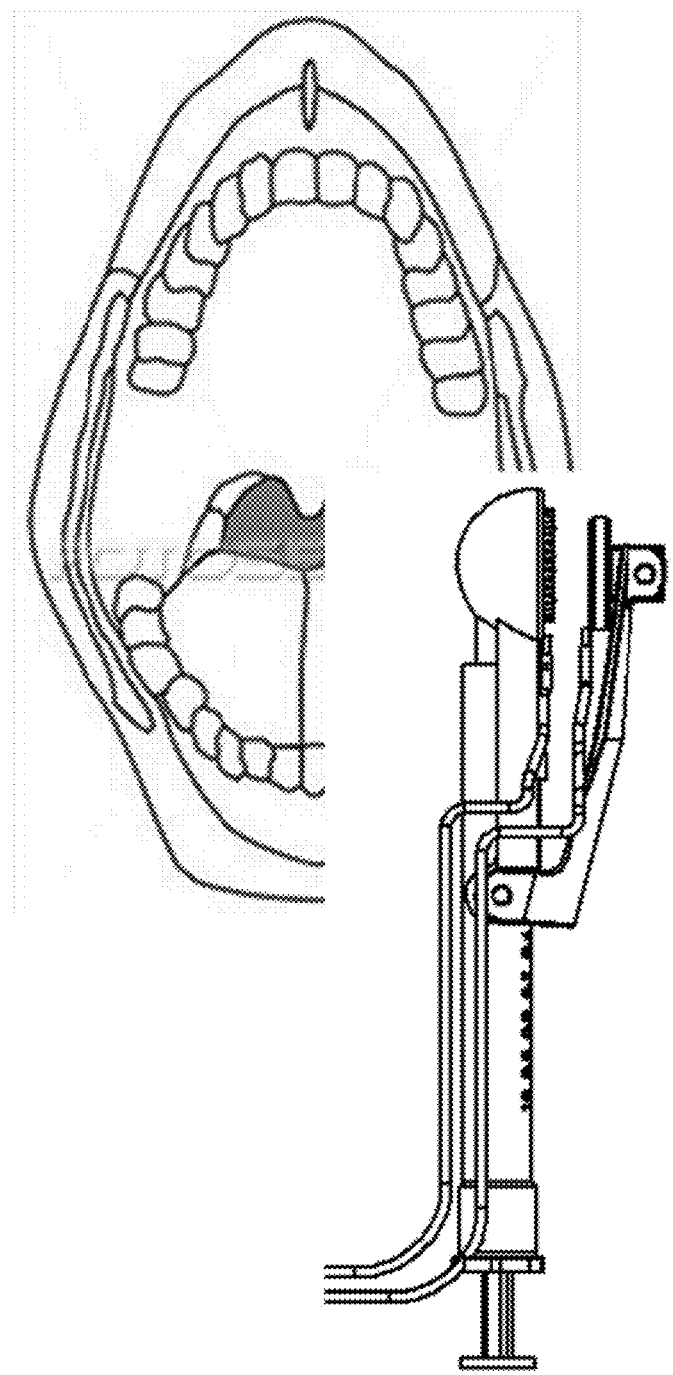
FIG. 17 shows the OM-I/EP device in relation to an open mouth.
Figure 18A:
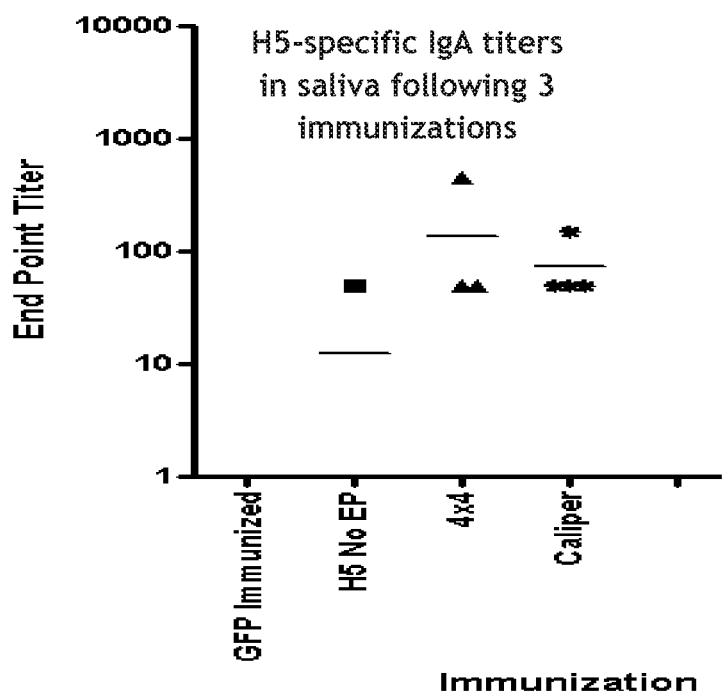
FIG. 18 displays graphs showing IgA titers in a) Saliva; b) Stool; c) Blood.
Figure 18B:
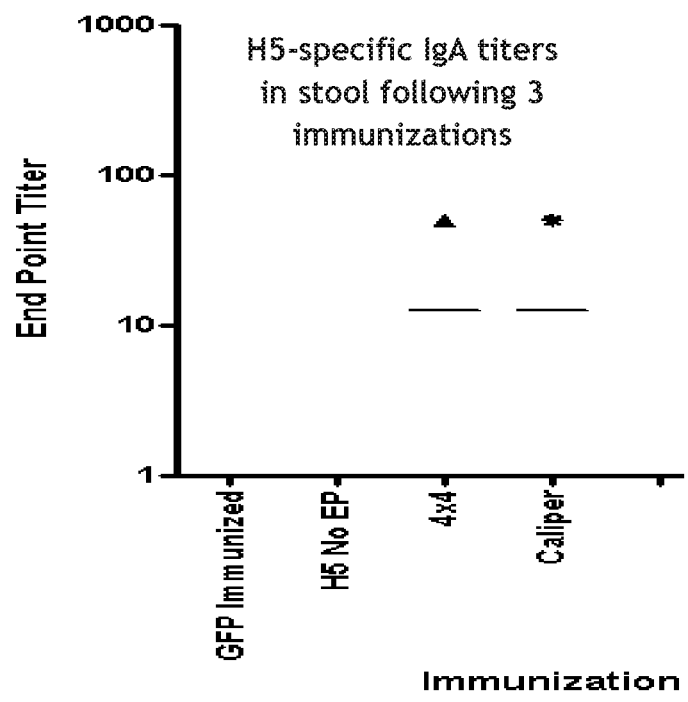
Figure 18C:
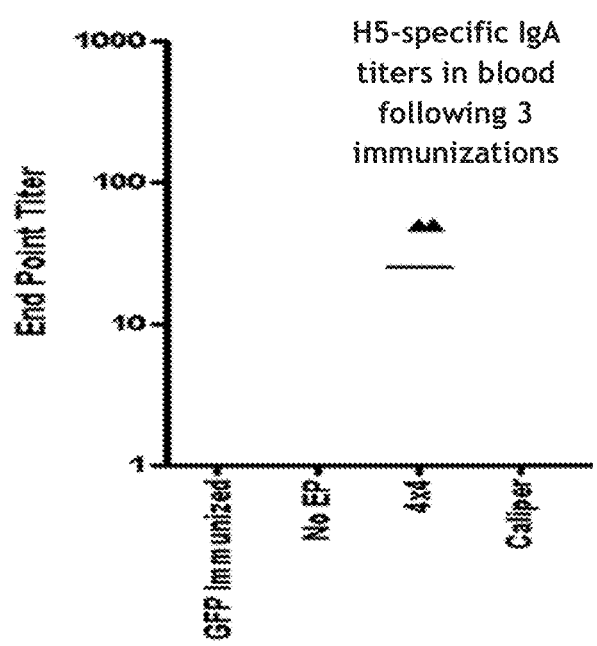

The OM-I/EP device has a main electrode micro needle plate (item #3 & FIG. 15) fastened to the head of a main housing (item #1). A voltage return electrode plate (item #4) and arm (items #5 and #6) is placed adjacent and outside the mouth. The main housing (item #1) can be mounted to a standard 1-ml lure-lock syringe (item #8). In use, the micro needle plate array (item #3 & FIG. 15) is placed on the inside of the mouth in intimate contact with the buccal mucosal lining (inner surface of cheek). The voltage return electrode (item #4) would be in contact with the outside adjacent surface of the cheek. The micro needle plate array (item #3 & FIG. 15), main housing (item #1) and the attached syringe (item #8) form the injection/electroporation device. The design of the large micro needle array allows for the injection of DNA vaccine over a large area. The small size and short length of the micro needles places the DNA vaccine to a controlled specific depth. A piston (item #2) and its sealing o-ring (item #9) form a common manifold area and driver that will insure even distribution of DNA vaccine through the micro-needle plate (item #3 & FIG. 15).

The requirement for the main electrode (item #3 & FIG. 15) is that they have many micro-needles of a specific length and diameter. The electrode must also, be made from electrically conductive materials (such as gold/silver plated brass or copper, stainless steel and/or titanium). The DNA vaccine must be placed in the upper most layers of the mucosa membranes. The main electrode (item #3 & FIG. 15) can be made by a few manufacturing techniques: such as Chemical etching, Electrical Discharge machining (EDM) and Electro-less nickel plating on a sacrificial pattern. The main housing and support parts could be made from injection molded materials (such as ABS, Polycarbonate and Polyolefin).

FIGS. 4-8 show results that support the following:

Optimized SIV DNA constructs+EP elicited IFN-g (~12,000 SFC/106) and proliferative CD8+ T cell responses (~20%) (no difference with CTACK). These responses were highest following the 4th immunization.

The addition of optimized CTACK DNA did not further enhance the induced response in the periphery by:

- IFN-g ELISpot
- CFSE Proliferation
- PBMC cytokine secretion
- IgA in the sera The addition of optimized CTACK DNA changes the phenotype of the response in the mucosa as measured by:

- BAL cytokine secretion
- More Polyfunctional CD8+ T cells
- Higher Frequencies of responding CD4+ and CD8+ T Cells
- IgA in Fecal & BAL samples

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Experiments were performed to assess IgA titers in the blood, nasal secretions, saliva and stools of animals immunized via an EP enhanced mucosal (orally) route with Influenza HA antigens. Significant IgA titers observed in the saliva is indicative of a mucosal immune response being successfully raised in a local mucosal region. Detection of IgA responses in the stool samples indicates a mucosal response at a distant site was raised. Detection of IgA titers in the blood sera suggests a systemic response was also raised.

H5 IgA ELISA

Following three mucosal EP-enhanced immunizations, positive H5 specific IgA titers were observed in the saliva of 3 out of 4 animal's electroporated with the 4×4 device (Inovio Pharmaceuticals, Inc., Blue Bell, Pa.) and 4 out of 4 animals electroporated with a caliper electroporation device. One animal was positive in the injection only group. See FIGS. 18*a*-18*c*.

Two animals had target specific positive IgA titers in their blood samples following three immunizations with the 4×4 device.

One animal from both the 4×4 device and caliper groups had target specific IgA responses in their stools.

None of the negative controls or injection only group animals had positive IgA stool or blood samples.

What is claimed is:

1. A device for electroporating cells of a mucosal membrane of a mammal, wherein the device comprises:

an electrode microneedle plate, wherein said electrode microneedle plate comprises a plurality of microneedles configured to contact the mucosal membrane and deliver at least one pulse of electrical energy having an electrical potential sufficient to electroporate said cells, a voltage return electrode positioned across from the electrode microneedle plate, wherein the voltage return electrode and the electrode microneedle plate are configured to be on opposite sides of the mucosal membrane, a main housing in physical communication with said electrode microneedle plate and voltage return electrode, wherein the main housing is in fluid communication with a syringe capable of storing a pharmaceutical formulation for delivery through the electrode microneedle plate;

a piston in physical communication between the main housing and the electrode microneedle plate, the piston located remote from the syringe and interposed between the syringe and the electrode microneedle plate, wherein the piston is actuatable so as to distribute the pharmaceutical formulation through the electrode microneedle plate, and an energy source in electrical communication with said electrode microneedle plate and said voltage return electrode, wherein the energy source is capable of generating said electric potential and delivering said electric potential to said cells through said electrode microneedle plate and said voltage return electrode.

2. The device according to claim 1, wherein the syringe is capable of storing the pharmaceutical formulation for delivery via the microneedles.

3. The device according to claim 2, wherein the microneedles of said electrode microneedle plate are made from electrically conductive materials comprising gold and silver plated brass, gold and silver plated copper, stainless steel, or titanium.

4. The device according to any one of claims 2 or 3, wherein said piston is actuatable so as to cause even distribution of said pharmaceutical formulation through said electrode microneedle plate.

5. The device according to any one of claims 2 or 3, wherein said energy source is capable of delivering through said electrode microneedle plate to said cells of the mucosal membrane at least one pulse of electrical energy having characteristics of between 1V and 30V, 2 mA and 100 mA, or 1 mS and 250 mS.

6. The device according to any one of claims 2 or 3, wherein said mucosal membrane comprises buccal, nasal, esophageal, rectal, vaginal, vulva, intestinal, bowel, stomach, bladder, urinary tract, or eye tissue.

7. The device of claim 1, wherein the main housing includes an arm moveable with respect to the electrode microneedle plate, and wherein the electrode microneedle plate is coupled to the main housing and the voltage return electrode is coupled to the arm.

8. The device according to claim 1, wherein the piston faces the electrode microneedle plate so as to define a manifold area therebetween, and the piston is configured to drive the pharmaceutical formulation through the electrode microneedle plate.

9. The device according to claim 8, wherein the piston is configured to drive an even distribution of the pharmaceutical formulation through the electrode microneedle plate.

10. The device according to claim 9, wherein the piston carries a sealing o-ring in contact with an interior of the main housing.

11. The device according to claim 1, wherein the main housing is configured to be locked to the syringe.

12. The device according to claim 11, wherein the main housing and the syringe collectively define a luer lock.

13. A method of administering a pharmaceutical formulation to cells of a mucosal membrane of a mammal with said device according to claim 1, said method comprising:
    contacting said electrode microneedle plate to said mucosal membrane,
    delivering said pharmaceutical formation to said mucosal membrane, and
    applying an electroporation-causing electrical pulse to said mucosal membrane through said electrode microneedle plate, wherein the electroporation-causing electrical pulse was generated by said energy source.

14. The method according to claim 13, wherein said contacting step comprises contacting said electrode microneedle plate to an inner surface of a mouth of said mammal.

15. The method according to claim 13, wherein said applying step comprises applying an electroporation-causing electrical pulse having characteristics of between 1V and 30V, 2 mA and 100 mA, or 1 mS and 250 mS.

* * * * *